(12) United States Patent
Ueno et al.

(10) Patent No.: US 11,557,189 B2
(45) Date of Patent: Jan. 17, 2023

(54) INFORMATION PROCESSING APPARATUS, INFORMATION PROCESSING METHOD, AND SYSTEM

(71) Applicant: Toyota Jidosha Kabushiki Kaisha, Toyota (JP)

(72) Inventors: Takaharu Ueno, Nagoya (JP); Yu Nagata, Chofu (JP); Yurika Tanaka, Yokosuka (JP); Ryosuke Kobayashi, Nagakute (JP); Shintaro Matsutani, Kariya (JP); Syouta Komatsu, Toyota (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 0 days.

(21) Appl. No.: 17/409,149

(22) Filed: Aug. 23, 2021

(65) Prior Publication Data
US 2022/0068107 A1 Mar. 3, 2022

(30) Foreign Application Priority Data
Aug. 25, 2020 (JP) .............................. JP2020-141739

(51) Int. Cl.
| G08B 21/04 | (2006.01) |
| A61B 5/01 | (2006.01) |
| A61B 5/11 | (2006.01) |
| A61B 5/00 | (2006.01) |

(52) U.S. Cl.
CPC ........ *G08B 21/0453* (2013.01); *A61B 5/0077* (2013.01); *A61B 5/01* (2013.01); *A61B 5/1117* (2013.01); *G08B 21/043* (2013.01); *G08B 21/0476* (2013.01)

(58) Field of Classification Search
CPC .................................................. G08B 21/0453
See application file for complete search history.

(56) References Cited

U.S. PATENT DOCUMENTS

| 2005/0242928 A1* | 11/2005 | Kirkeby ................... G08B 5/22 340/286.07 |
| 2017/0135587 A1* | 5/2017 | Desroches ............. G16H 20/30 |

FOREIGN PATENT DOCUMENTS

JP 2018-093977 A 6/2018

* cited by examiner

*Primary Examiner* — Travis R Runnings
(74) *Attorney, Agent, or Firm* — Dinsmore & Shohl LLP

(57) ABSTRACT

There is provided a controller that performs: determining, based on information obtained from a sensor configured to detect a physical condition of a target person, which of a plurality of predetermined categories the physical condition of the target person falls into; and transmitting a notification corresponding to the physical condition of the target person to a terminal of a notification destination that corresponds to a category into which the physical condition of the target person is determined to fall, wherein terminals of notification destinations are set for the plurality of categories, respectively.

13 Claims, 11 Drawing Sheets

| TARGET PERSON ID | NOTIFICATION DESTINATION | | | |
|---|---|---|---|---|
| | FIRST CATEGORY | SECOND CATEGORY | THIRD CATEGORY | SPECIFIC USER TERMINAL |
| × × × | × × × | × × × | × × × | × × × |
| | × × × | | | |
| × × × | × × × | × × × | × × × | × × × |
| × × × | × × × | × × × | × × × | × × × |
| . . . | . . . | . . . | . . . | . . . |

Fig. 4

| PHYSICAL CONDITION | CATEGORY | | |
|---|---|---|---|
| | 1 | 2 | 3 |
| BODY TEMPERATURE (A1 - A2) | ○ | | |
| BODY TEMPERATURE (A2 - A3) | | ○ | |
| BODY TEMPERATURE (A3 -) | | | ○ |
| INJURY (LIGHT) | ○ | | |
| INJURY (MEDIUM) | | ○ | |
| INJURY (HEAVY) | | | ○ |
| ... | ... | ... | ... |

Fig. 5

| NOTIFICATION DESTINATION ID | POSITION | SCHEDULE | NOTIFICATION DESTINATION |
|---|---|---|---|
| x x x | x x x | x x x | x x x |
| x x x | x x x | x x x | x x x |
| x x x | x x x | x x x | x x x |
| . . . | . . . | . . . | . . . |

Fig. 6

INFORMATION PROCESSING APPARATUS, INFORMATION PROCESSING METHOD, AND SYSTEM

CROSS REFERENCE TO THE RELATED APPLICATION

This application claims the benefit of Japanese Patent Application No. 2020-141739, filed on Aug. 25, 2020, which is hereby incorporated by reference herein in its entirety.

BACKGROUND

Technical Field

The present disclosure relates to an information processing apparatus, an information processing method, and a system.

Description of the Related Art

There has been disclosed a technology in which biological information of a person to be monitored is obtained by a wearable terminal, and when it is determined based on an analysis result of the biological information that the person is in an abnormal state, the terminal of the person to be monitored is notified of the determination (for example, Patent Literature 1).

CITATION LIST

Patent Literature

Patent Literature 1: Japanese Patent Application Laid-Open Publication No. 2018-093977

SUMMARY

An object of the present disclosure is to notify an appropriate party when an abnormality occurs in the physical body of a target person.

One aspect of the present disclosure is directed to an information processing apparatus including a controller configured to perform:

determining, based on information obtained from a sensor configured to detect a physical condition of a target person, which of a plurality of predetermined categories the physical condition of the target person falls into; and transmitting a notification corresponding to the physical condition of the target person to a terminal of a notification destination that corresponds to a category into which the physical condition of the target person is determined to fall, wherein terminals of notification destinations are set for the plurality of categories, respectively.

Another aspect of the present disclosure is directed to an information processing method for causing a computer to perform:

determining, based on information obtained from a sensor configured to detect a physical condition of a target person, which of a plurality of predetermined categories the physical condition of the target person falls into; and transmitting a notification corresponding to the physical condition of the target person to a terminal of a notification destination that corresponds to a category into which the physical condition of the target person is determined to fall, wherein terminals of notification destinations are set for the plurality of categories, respectively.

A further aspect of the present disclosure is directed to a system comprising:

a storage unit configured to store a relationship between a physical condition of a target person and a plurality of categories and a relationship between the plurality of categories and terminals of notification destinations;

a sensor configured to detect the physical condition of the target person; and a controller configured to perform:

determining, based on information obtained from the sensor, which of the plurality of categories the physical condition of the target person falls into; and transmitting a notification corresponding to the physical condition of the target person to a terminal of a notification destination that corresponds to a category into which the physical condition of the target person is determined to fall.

In addition, a still further aspect of the present disclosure is directed to a program for causing a computer to perform the information processing method, or a computer-readable storage medium storing the program in a non-transitory manner.

According to the present disclosure, it is possible to notify an appropriate party when an abnormality has occurred in the body of the target person.

BRIEF DESCRIPTION OF THE DRAWINGS

FIG. 4 is a diagram illustrating an example of a table structure of a target person DB;

FIG. 5 is a diagram illustrating an example of a table structure of a category DB;

FIG. 6 is a diagram illustrating an example of a table structure of a notification destination DB;

DESCRIPTION OF THE EMBODIMENTS

Figure 1:
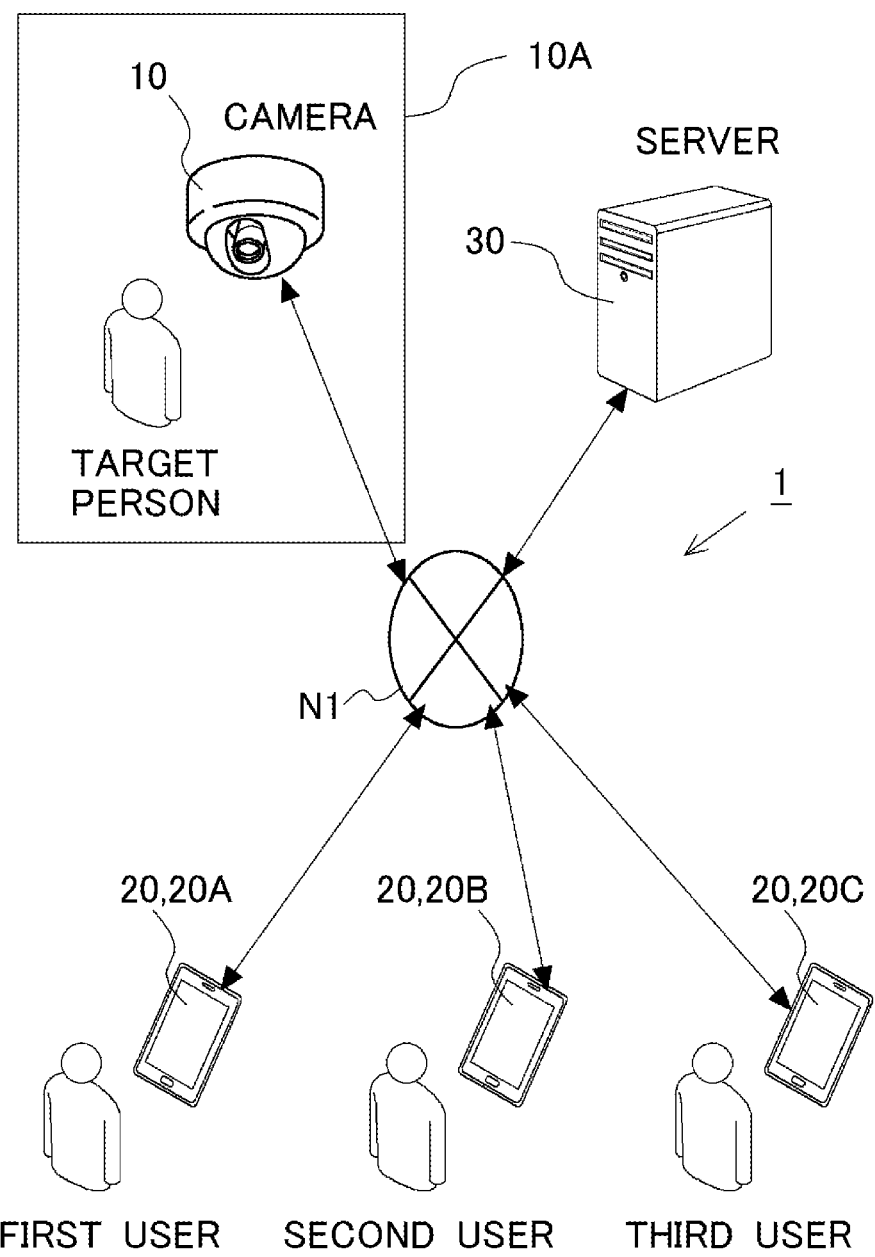
FIG. 1 is a diagram illustrating a schematic configuration of a system according to an embodiment.

An information processing apparatus, which is one aspect of the present disclosure, is provided with a controller. The controller performs: determining, based on information obtained from a sensor configured to detect a physical condition of a target person, which of a plurality of predetermined categories the physical condition of the target person falls into; and transmitting a notification corresponding to the physical condition of the target person to a terminal of a notification destination that corresponds to a category into which the physical condition of the target person is determined to fall, wherein terminals of notification destinations are set for the plurality of categories, respectively. The target person is a user to be monitored. The target person is, for example, a child, an elderly person, or a care-requiring person. Then, the target person is also a user who is monitored to see which of the plurality of predetermined categories the physical condition of the user falls into. The physical condition of the user is sensed by the sensor. The sensor is, for example, an image sensor that takes an image of the target person, or a sensor that measures the pulse, blood pressure, respiration, or body temperature of the target person. This sensor may be either a contact type sensor or a non-contact type sensor. The sensor is not limited as long as it detects the physical condition of the user.

The plurality of categories may be, for example, categories into which the physical condition of the target person is classified. The controller may determine which of the plurality of predetermined categories the physical condition of the target person falls into, and when the physical condition of the target person does not fall into any category, the controller may do nothing. In addition, for example, by comparing information about a detection value of the sensor corresponding to each category that has been stored in advance with information actually obtained from the sensor, the controller may determine which of the plurality of categories the physical condition of the target person falls into.

A notification destination terminal is set for each of the plurality of categories. The notification destination can be, for example, a user who responds when the physical condition of the target person is bad, a user who goes and sees the state of the target person, a guardian of the target person (i.e., may be a person who has an obligation to guard or protect the target person), a user who arranges an ambulance, or the like. The notification destination terminal is, for example, one of the terminals possessed by these users. The notification destination terminal receives a notification corresponding to the physical condition of the target person. This notification may be, for example, a notification of the physical condition of the target person or a request for some action. The terminal that has received this notification may make a display about the notification on its screen, for example. In this way, when an abnormality occurs in the body of the target person, a notification is transmitted to the terminal of the notification destination corresponding to the physical condition of the target person, thus making it possible to notify a more appropriate party of the fact that the abnormality has occurred in the body of the target person.

Hereinafter, embodiments of the present disclosure will be described based on the accompanying drawings. The configurations of the following embodiments are examples, and the present disclosure is not limited to the configurations of the embodiments. In addition, the following embodiments can be combined with one another as long as such combinations are possible and appropriate.

First Embodiment

FIG. 1 is a diagram illustrating a schematic configuration of a system 1 according to a first present embodiment. In the example of FIG. 1, the system 1 includes a camera 10 arranged in an observation or monitoring space 10A in which a target person is monitored, three user terminals 20, and a server 30. Here, note that a user terminal 20 used by a first user is referred to as a first user terminal 20A, a user terminal 20 used by a second user is referred to as a second user terminal 20B, and a user terminal 20 used by a third user is referred to as a third user terminal 20C. In the following, in cases where the first user, the second user and the third user are not distinguished from one another, they are simply referred to as users. Also, in cases where the first user terminal 20A, the second user terminal 20B and the third user terminal 20C are not distinguished from one another, they are simply referred to as user terminals 20. Note that a user corresponding to each terminal does not necessarily exist. For example, in cases where an ambulance is arranged by a program installed in a user terminal 20 that has received a notification, the user corresponding to the user terminal 20 is not necessary.

The first user terminal 20A, the second user terminal 20B, and the third user terminal 20C are terminals that receive notifications according to the physical condition of the target person. For example, in cases where the target person becomes ill or injured, the degree of illness or injury may be classified into three categories: "light", "medium", and "heavy", wherein the first user terminal 20A may be a user terminal 20 corresponding to the "light" category, the second user terminal 20B may be a user terminal 20 corresponding to the "medium" category, and the third user terminal 20C may be a user terminal 20 corresponding to the "heavy" category. In addition, the third user terminal 20C may be a terminal that is carried by an ambulance crew, a terminal that is used for arranging emergency transportation, or a terminal in a hospital.

In the following description, it is assumed that the physical condition of the target person is classified into "no problem", "first category", "second category", or "third category", wherein the first user terminal 20A corresponds to the first category, the second user terminal 20B corresponds to the second category, and the third user terminal 20C corresponds to the third category. "No problem" indicates a state in which there is no abnormality in the body of the target person, and any user terminal 20 does not correspond thereto. The "first category" is a category corresponding to a case where the symptoms of illness or injury of the target person are relatively light or mild. The "second category" is a category corresponding to a case where the symptoms of the illness or injury of the target person are heavier than the first category and lighter than the third category. The "third category" is a category corresponding to a case where the symptoms of the illness or injury of the target person are heavier than the second category. The third category may be a category in which the target person needs to be transported to a hospital. That is, the third category may be a category corresponding to the transport of the target person to a hospital.

The server 30 obtains images from the camera 10. By analyzing the images taken by the camera 10, the server 30 can detect the physical condition of the target person. The camera 10 is arranged so as to take pictures or images of the monitoring space 10A. The monitoring space 10A is, for example, a room in which the target person usually spends or a living room in a house. The monitoring space 10A can include a plurality of rooms. Note that the camera 10 may be a thermal camera that detects the body surface temperature of the target person. In this case, the server 30 detects the body surface temperature (hereinafter also referred to as the body temperature) of the target person. The server 30 may detect the physical condition of the target person based on the images taken by the camera 10. By analyzing the images taken by the camera 10, the server 30 may detect, for example, that the walking of the target person is unsteady, the target person has fallen, or the target person has tumbled. In addition, the respiration rate or the heart rate of the target person may be detected based on the images taken by the camera 10. In the present embodiment, the camera 10 is described as an example of the sensor that detects the physical condition of the target person, but another sensor may be employed.

The camera 10, the user terminals 20, and the server 30 are connected to one another by a network N1. The network N1 is, for example, a worldwide public communication network such as the Internet, and a WAN (wide area network) or other communication networks may be adopted. In addition, the network N1 may include a telephone communication network such as a mobile phone network or the like, or a wireless communication network such as Wi-Fi (registered trademark) or the like. Here, note that FIG. 1 illustrates three user terminals 20 by way of example, but there can be a plurality of user terminals 20.

Figure 2:
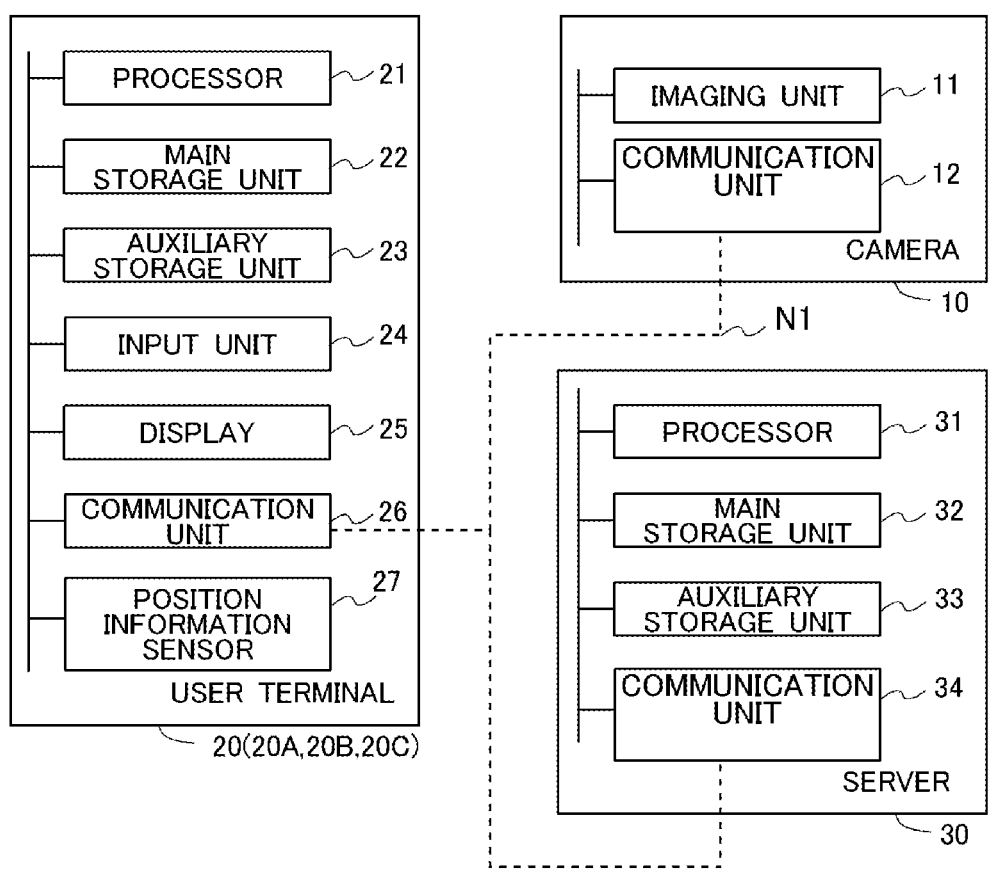
FIG. 2 is a block diagram schematically illustrating an example of a configuration of each of a camera, a user terminal and a server, which together constitute the system according to the embodiment.

Hardware configurations and functional configurations of the camera 10, the user terminals 20 and the server 30 will be described based on FIG. 2. FIG. 2 is a block diagram schematically illustrating one example of the configuration of each of the camera 10, the user terminals 20 and the server 30, which together constitute the system 1 according to the present embodiment.

The server 30 has a configuration of a general computer. The server 30 includes a processor 31, a main storage unit 32, an auxiliary storage unit 33, and a communication unit 34. These components are connected to one another by a bus. The processor 31 is an example of a controller.

The processor 31 is a CPU (Central Processing Unit), a DSP (Digital Signal Processor), or the like. The processor 31 controls the server 30 thereby to perform various information processing operations. The main storage unit 32 is a RAM (Random Access Memory), a ROM (Read Only Memory), or the like. The auxiliary storage unit 33 is an EPROM (Erasable Programmable ROM), a hard disk drive (HDD), a removable medium, or the like. The auxiliary storage unit 33 stores an operating system (OS), various programs, various tables, and the like. The processor 31 loads a program stored in the auxiliary storage unit 33 into a work area of the main storage unit 32 and executes the program, so that each component or the like is controlled through the execution of the program. Thus, the server 30 realizes functions matching predetermined purposes, respectively. The main storage unit 32 and the auxiliary storage unit 33 are computer-readable recording media. Here, note that the server 30 may be a single computer or a combination of a plurality of computers. In addition, the information stored in the auxiliary storage unit 33 may be stored in the main storage unit 32. Also, the information stored in the main storage unit 32 may be stored in the auxiliary storage unit 33. The main storage unit 32 or the auxiliary storage unit 33 is an example of a storage unit.

The communication unit 34 is a unit that communicates with the user terminals 20 via the network N1. The communication unit 34 is, for example, a LAN (Local Area Network) interface board, a radio or wireless communication circuit for radio or wireless communication, or the like. The LAN interface board or the wireless communication circuit is connected to the network N1.

Then, the camera 10 is a device that is arranged indoors or outdoors so as to take pictures or images of the surroundings thereof. The camera 10 is provided with an imaging unit 11 and a communication unit 12. The imaging unit 11 takes pictures or images by using an imaging element such as a CCD (Charge Coupled Device) image sensor, a CMOS (Complementary Metal Oxide Semiconductor) image sensor or the like. The images obtained by photographing may be either still images or moving images.

The communication unit 12 is a communication unit for connecting the camera 10 to the network N1. The communication unit 12 is, for example, a circuit for communicating with other devices (e.g., the server 30 or the like) via the network N1 by making use of a radio or wireless communication such as a mobile communication service (e.g., a telephone communication network such as 5G (5th Generation), 4G (4th Generation), 3G (3rd Generation), LTE (Long Term Evolution) or the like), Wi-Fi (registered trademark), Bluetooth (registered trademark) or the like. The images taken by the camera 10 are transmitted to the server 30 through the communication unit 12.

Now, the user terminal 20 will be described. The user terminal 20 is, for example, a smart phone, a mobile phone, a tablet terminal, a personal information terminal, a wearable computer (such as a smart watch or the like), or a small computer such as a personal computer (PC). The user terminal 20 includes a processor 21, a main storage unit 22, an auxiliary storage unit 23, an input unit 24, a display 25, a communication unit 26, and a position information sensor 27. These components are connected to one another by a bus. The processor 21, the main storage unit 22 and the auxiliary storage unit 23 are the same as the processor 31, the main storage unit 32 and the auxiliary storage unit 33 of the server 30, respectively, and hence, the description thereof will be omitted.

The input unit 24 is a unit that receives an input operation performed by the user, and is, for example, a touch panel, a mouse, a keyboard, a push button, or the like. The display 25 is a unit that presents information to the user, and is, for example, an LCD (Liquid Crystal Display), an EL (Electroluminescence) panel, or the like. The input unit 24 and the display 25 may be configured as a single touch panel display. The communication unit 26 is a communication unit for connecting the user terminal 20 to the network N1. The communication unit 26 is, for example, a circuit for communicating with other devices (e.g., the server 30 and the like) via the network N1 by making use of a radio or wireless communication network such as a mobile communication service (e.g., a telephone communication network such as 5G (5th Generation), 4G (4th Generation), 3G (3rd Generation), LTE (Long Term Evolution) or the like), Wi-Fi (registered trademark), Bluetooth (registered trademark) or the like.

The position information sensor 27 obtains position information (e.g., latitude and longitude) of the user terminal 20 at predetermined intervals. The position information sensor 27 is, for example, a GPS (Global Positioning System) receiver unit, a wireless communication unit or the like. The information obtained by the position information sensor 27 is recorded, for example, in the auxiliary storage unit 23 or the like, and transmitted to the server 30.

Figure 3:
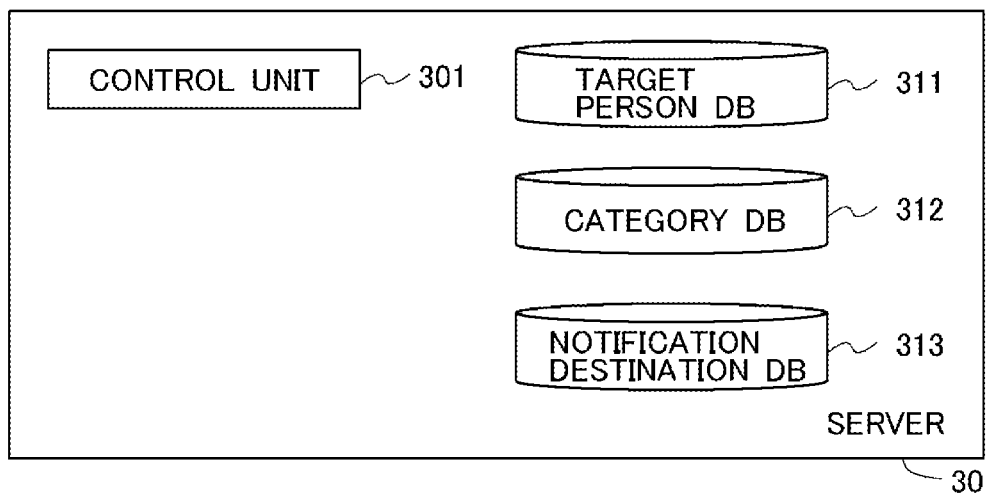
FIG. 3 is a diagram illustrating an example of a functional configuration of the server.

Next, the functions of the server 30 will be described. FIG. 3 is a view illustrating an example of a functional configuration of the server 30. The server 30 includes, as functional components, a control unit 301, a target person DB 311, a category DB 312, and a notification destination DB 313. The processor 31 of the server 30 executes the processing of the control unit 301 by a computer program on the main storage unit 32. The target person DB 311, the category DB 312, and the notification destination DB 313 are built by a program of a database management system (DBMS) that is executed by the processor 31 to manage data stored in the auxiliary storage unit 33. The target person DB 311, the category DB 312, and the notification destination DB 313 are, for example, relational databases. Here, note that any of the individual functional components of the server 30 or a part of the processing thereof may be executed by another computer connected to the network N1.

The control unit 301 obtains target person information that is information about a notification destination at the time when an abnormality has occurred in the body of the target person, category information that is information about a category corresponding to the physical condition of the target person, and notification destination information indicating the state of the notification destination. The target person information, the category information, and the notification destination information are transmitted, for example, from the user terminal 20. Upon obtaining the target person information, the category information, and the notification destination information, the control unit 301 stores the target person information, the category information, and the notification destination information in the target person DB 311, the category DB 312, and the notification destination DB 313, respectively.

The target person information includes, for example, information about a notification destination corresponding to each target person. The notification destination is set for each category. A plurality of notification destinations may be registered for one category. FIG. 4 is a diagram illustrating an example of a table configuration of the target person DB 311. A target person information table includes fields of target ID, first category, second category, third category, and specific user terminal.

The target person ID field is a field where identification information unique to each target person is entered. A target person ID is assigned to each target person by the control unit 301. The first category field is a field in which information about each notification destination in the case where the physical condition of each target person falls into the first category is entered. The information about each notification destination includes, for example, a notification destination ID, which will be described later. Here, note that the information about each notification destination may include information indicating, for example, an e-mail address, a telephone number, or an SNS account. The second category field is a field in which information about each notification destination in the case where the physical condition of each target person falls into the second category is entered. Also, the third category field is a field in which information about each notification destination in the case where the physical condition of each target person falls into the third category is entered. Note that the number of notification destinations corresponding to each category is not limited to one. The information entered into the first category field, the second category field, and the third category field may have been registered in advance via a user terminal 20 possessed or carried by a guardian of a target person, for example. The specific user terminal field is a field in which the notification destination ID of each user terminal 20 (specific user terminal 20) to be notified when a problem occurs in the body of each target person is entered. The specific user terminal 20 is, for example, a user terminal 20 possessed or carried by the guardian of the target person.

Then, the category information will be described. The category information includes, for example, information indicating into which category the physical condition of a target person falls. FIG. 5 is a diagram illustrating an example of a table configuration of the category DB 312. The category corresponding to the physical condition is entered into the category DB 312. Note that the category corresponding to the physical condition may be different for each target person or may be common to all target persons. In addition, the category corresponding to the physical condition may be determined by a guardian or the like of a target person, or may be determined by the control unit 301. Therefore, the category information may be transmitted from a user terminal 20 or may be generated by the control unit 301.

Next, the notification destination information will be described. The notification destination information includes, for example, information about the state of a notification destination corresponding to each category. Examples of the information about the state of the notification destination include position information and information about a schedule. FIG. 6 is a diagram illustrating an example of a table configuration of the notification destination DB 313. The notification destination information table includes fields of notification destination ID, position, schedule, and notification destination.

The notification destination ID field is a field in which identification information unique to each user terminal 20 to be registered as its notification destination is entered. A user ID is assigned to each user terminal 20 by the control unit 301. Note that a notification destination ID may be identification information of a user who possesses his or her user terminal 20. The position field is a field in which position information of a user terminal 20 transmitted from the user terminal 20 is entered. The schedule field is a field in which information about a schedule of a user transmitted from his or her user terminal 20 is entered. For example, in cases where an application for managing the schedule of the user is installed in his or her user terminal 20, a schedule entered into the application is transmitted from the user terminal 20 to the server 30. The notification destination field is a field in which information about a notification destination corresponding to each notification destination ID is entered. The information about the notification destination includes, for example, information indicating an e-mail address, a telephone number, or an SNS account.

In addition, upon receiving an image from the camera 10, the control unit 301 analyzes the image thereby to determine the physical condition of a target person. The control unit 301 may determine the physical condition of the target person by analyzing the motion of the target person, for example. Note that the control unit 301 may specify the target person by analyzing the image from the camera 10, or may regard a person appearing in the image as the target person. For example, the control unit 301 may detect a heart rate, a body temperature, a respiratory rate, or the like by analyzing the image taken by the camera 10. Then, the control unit 301 determines whether or not the physical condition of the target person falls into any one of the following categories: no problem, the first category, the second category, and the third category. A relationship between the physical condition of the target person and the categories has been stored in advance as illustrated in FIG. 5.

When the physical condition of the target person falls into any one of the first category, the second category, and the third category, the control unit 301 transmits a notification to a notification destination corresponding to the category thus determined. At this time, for example, the notification may be transmitted together with the images taken by the target person. The notification destination is selected based on the target person DB 311 illustrated in FIG. 4 and the determined category.

Here, note that in cases where a plurality of notification destinations have been registered in each category, the control unit 301 may transmit a notification to each of the plurality of notification destinations, or may transmit a notification to a notification destination selected from among the plurality of notification destinations. The selection of the notification destination(s) may be made according to the priority of the notification destinations, for example. The priority of each notification destination may have been set in advance by the user. Then, a notification may be transmitted to a user having the highest priority among the plurality of users, or the priority may be digitized so that a notification can be transmitted to a notification destination having a priority equal to or higher than a predetermined value. Also, the selection of the notification destination(s) may be made based on the current situations of the notification destinations. In this case, for example, a notification may be made based on the position information or the information about schedule corresponding to a notification destination ID illustrated in FIG. 6. For example, a notification destination whose current location is closest to the target person may be selected from among a plurality of notification destinations. The position of the monitoring space 10A, which is the current position of the target person, has been stored in advance in the auxiliary storage unit 33. In addition, for example, a user whose schedule corresponding to a notification destination is free may be selected. Moreover, a user may also be selected who is capable of changing his or her schedule even if there is no room in the schedule. Further, for example, the priority of each notification destination may be calculated based on the position information and schedule-related information thereof, and a notification may be made to a notification destination with the highest priority, or a notification may be made to notification destinations with a priority equal to or higher than a predetermined value. For example, the priority may be calculated such that the closer the position of a user terminal 20 is to the target person, the higher the priority thereof becomes. Also, for example, the priority may be calculated so that the priority of a user terminal 20 whose schedule has not yet been entered at the current time is higher than the priority of a user terminal 20 whose schedule has already been entered.

Figure 7:
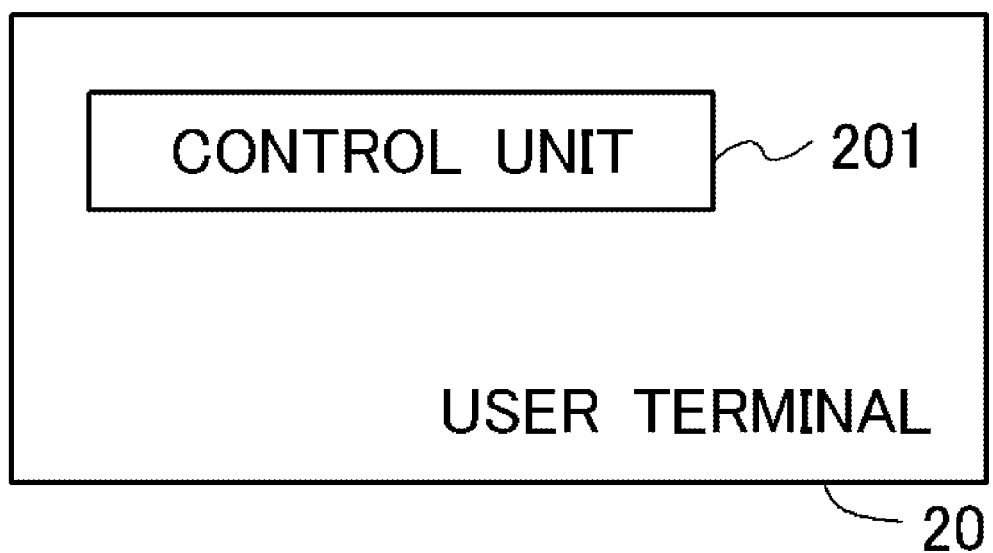
FIG. 7 is a diagram illustrating an example of a functional configuration of the user terminal.

Then, the functions of the user terminal 20 will be described. FIG. 7 is a view illustrating an example of a functional configuration of the user terminal 20. The user terminal 20 includes a control unit 201 as its functional component. The processor 21 of the user terminal 20 executes the processing of the control unit 201 by a computer program on the main storage unit 22.

The control unit 201 implements an application for managing the schedules of its user (hereinafter, also referred to as a scheduler). The scheduler is, for example, an application that stores the schedules entered by the user via the input unit 24 and notifies the user that the start time of each schedule approaches. When entering a schedule into the scheduler, the user enters a start time, an end time, a place (position), and a content.

In addition, the control unit 201 transmits the position information and the schedule information to the server 30 at predetermined time intervals. Note that it is not necessary to transmit the location information and the schedule information at the same time. The position information and the schedule information are transmitted in association with a notification destination ID. The control unit 201 transmits an output from the position information sensor 27 to the server 30 as the position information. Also, the control unit 201 obtains the schedule information from the scheduler and transmits it to the server 30.

Moreover, the control unit 201 displays, for example, the information received from the server 30 on the display 25. For example, upon receiving a notification from the server 30 about the physical condition of the target person, the control unit 201 displays the information corresponding to the notification. For example, a message such as "The target person has been injured", "The fever of the target person has increased", or "A problem has occurred with the target person" is displayed, or the images taken by the camera 10 are displayed.

Also, upon receiving a notification from the server 30, the control unit 201 displays a screen on the display 25 to allow the user to enter whether or not he or she agrees to go and see the state of the target person, for example. In addition, when the user enters via the input unit 24 whether or not to agree to go and see the target person, the information is transmitted to the server 30.

Figure 8:
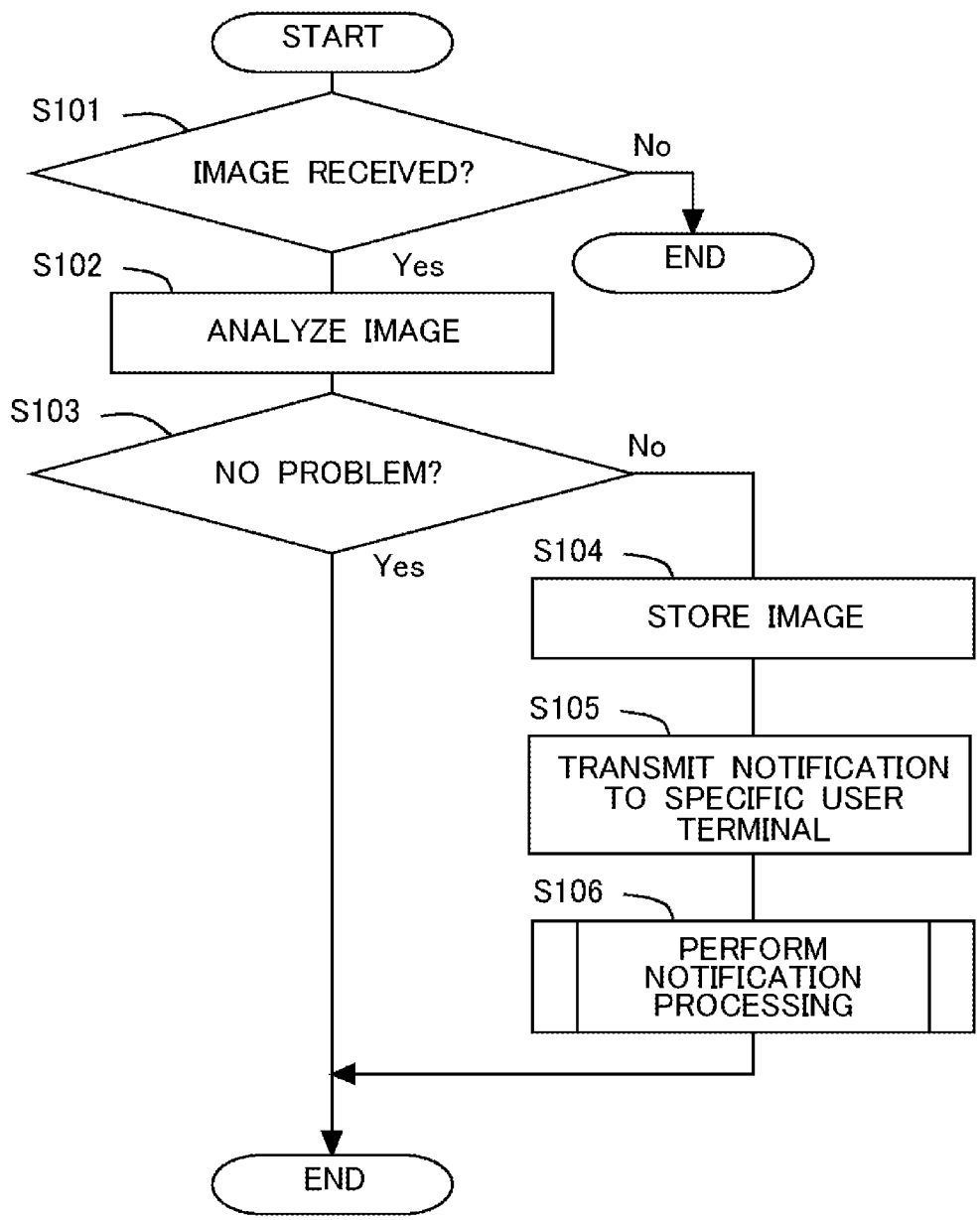
FIG. 8 is a flowchart of the processing of transmitting schedule information from the user terminal to the server according to the embodiment.

Next, the processing of the server 30 watching or monitoring the target person will be described. FIG. 8 is a flowchart of the processing in which the server 30 watches or monitors the target person. The processing illustrated in FIG. 8 is executed at predetermined time intervals in the server 30. Note that in the following description, it is assumed that the target person DB 311, the category DB 312, and the notification destination DB 313 have already been built. This routine is executed for each target person.

In step S101, the control unit 301 determines whether or not an image has been received from the camera 10. When an affirmative determination is made in step S101, the processing proceeds to step S102, whereas when a negative determination is made, this routine is ended. In step S102, the control unit 301 analyzes the received image to determine whether or not the physical condition of the target person falls into any of the following categories: no problem, the first category, the second category, and the third category. Then, in step S103, the control unit 301 determines, as a result of the image analysis, whether or not the physical condition of the target person falls into the category of "no problem". When an affirmative determination is made in step S103, this routine is ended because a notification to a destination is not necessary. On the other hand, when a negative determination is made in step S103, the processing proceeds to step S104.

In step S104, the control unit 301 stores the image received in step S101 in the auxiliary storage unit 33. The image thus stored is transmitted to a user terminal 20 together with a notification to be described later, for example. Here, even if a user who has received the notification goes and sees the state of the target person, symptoms such as illness may not be reproduced. In addition, in cases where the target person is transported to a hospital by ambulance, a situation in which an abnormality has occurred in the body of the target person may be determined from the image, which may be useful for diagnosis. For this purpose, the control unit 301 stores in the auxiliary memory 33 an image of the body of the target person when the abnormality has occurred therein. Note that the timing of storing the image is not limited to the step S104. For example, the image may be stored after it has been determined which category the physical condition of the target person falls into. At this time, the image may be stored in association with the category. After the image is stored in the auxiliary storage unit 33, the processing proceeds to step S105.

In step S105, the control unit 301 transmits a notification to a specific user terminal 20. The control unit 301 transmits the notification to the specific user terminal 20 based on the information stored in the target person DB 311 illustrated in FIG. 4 and the notification destination DB 313 illustrated in FIG. 6. The notification includes information indicating that a problem has occurred in the body of the target person. The timing of transmitting the notification to the specific user terminal 20 is not limited to the step S105. For example, after it is determined which category the physical condition of the target person falls into, the notification may be transmitted together with information indicating which category the physical condition of the target person falls into. Note that the notification to the specific user terminal 20 may not be transmitted. Then, in step S106, the control unit 301 executes notification processing.

Figure 9:
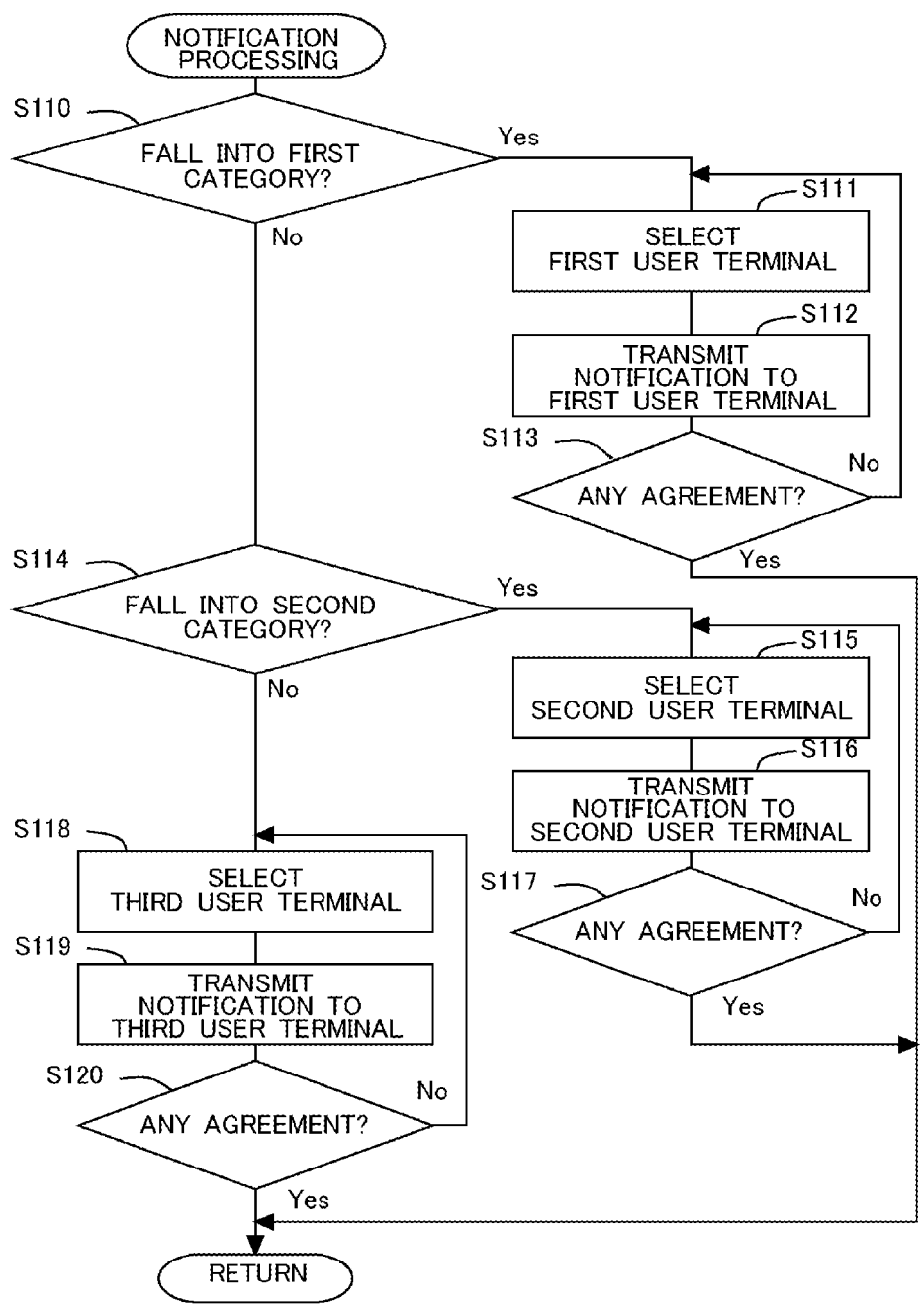
FIG. 9 is a flowchart of notification processing according to a first embodiment.

FIG. 9 is a flowchart of the notification processing according to the present embodiment. The notification processing illustrated in FIG. 9 corresponds to the processing of S105 in FIG. 8 that is executed in the server 30. In step S110, the control unit 301 determines whether or not the physical condition of the target person falls into the first category. When an affirmative determination is made in step S110, the processing proceeds to step S111.

In step S111, the control unit 301 selects a first user terminal 20A. In cases where only one first user terminal 20A corresponding to the target person has been registered, the control unit 301 selects the registered first user terminal 20A. On the other hand, in cases where a plurality of user terminals 20 have been registered for the first user terminal 20A, the control unit 301 selects, for example, a first user terminal 20A having the highest priority. Alternatively, the control unit 301 may select a plurality of first user terminals 20A having a priority equal to or higher than a predetermined value, or may select all the first user terminals 20A regardless of their priority.

In step S112, the control unit 301 transmits a notification to the selected first user terminal 20A. The notification includes information indicating that the physical condition of the target person falls into the first category.

In step S113, the control unit 301 determines whether or not an agreement has been obtained from the first user terminal 20A. For example, there may be a case where the first user who possesses or carries the first user terminal 20A may not be able to go and see the state of the target person for some reason. In this case, the first user carrying the first user terminal 20A may also be able to refuse to go and see the state of the target person. For example, the first user enters into the first user terminal 20A information indicating that he or she does not agree to go and see the state of the target person. Then, the information of disagreement is transmitted from the first user terminal 20A to the server 30. On the other hand, in cases where the first user agrees to go and see the state of the target person, information of the agreement is transmitted from the first user terminal 20A to the server 30. Here, note that, in step S113, in cases where a response is not obtained from the first user terminal 20A even after a predetermined time has elapsed from transmission of the notification, it may be treated as if an agreement was not obtained from the first user terminal 20A.

When an affirmative determination is made in step S113, this routine is ended. On the other hand, when a negative determination is made in step S113, the processing returns to step S111, where the control unit 301 selects another first user terminal 20A. At this time, the control unit 301 selects a new first user terminal 20A by excluding the first user terminal 20A that did not agree.

On the other hand, when a negative determination is made in step S110, the processing proceeds to step S114. In step S114, the control unit 301 determines whether or not the physical condition of the target person falls into the second category. When an affirmative determination is made in step S114, the processing proceeds to step S115. In step S115, the control unit 301 selects a second user terminal 20B in the same way as the selection of the first user terminal 20A in step S111. Then, in step S116, the control unit 301 transmits a notification to the second user terminal 20B thus selected. This notification includes information indicating that the physical condition of the target person falls into the second category.

In step S117, the control unit 301 determines whether or not an agreement has been obtained from the second user terminal 20B. When a second user agrees to go and see the state of the target person, information of the agreement is transmitted from the second user terminal 20B to the server 30. On the other hand, when the second user does not agree to go and see the state of the target person, information of the disagreement is transmitted from the second user terminal 20B to the server 30. When an affirmative determination is made in step S117, this routine is ended. On the other hand, when a negative determination is made in step S117, the processing returns to step S115, where the control unit 301 selects another second user terminal 20B. At this time, the control unit 301 selects a new second user terminal 20B by excluding the second user terminal 20B that did not agree.

On the other hand, when a negative determination is made in step S114, the processing proceeds to step S118. In step S118, the control unit 301 selects a third user terminal 20C. This selection is made in the same way as in step S111. Then, in step S119, the control unit 301 transmits a notification to the third user terminal 20C thus selected. This notification includes information indicating that the physical condition of the target person falls into the third category.

In step S120, the control unit 301 determines whether or not an agreement has been obtained from the third user terminal 20C. When an affirmative determination is made in step S120, this routine is ended. On the other hand, when a negative determination is made in step S120, the processing returns to step S118, where the control unit 301 selects another third user terminal 20C. At this time, the control unit 301 selects a new third user terminal 20C by excluding the third user terminal 20C that did not agree. Here, note that, in step S120, in cases where a response is not obtained from the third user terminal 20C even after a predetermined time has elapsed from transmission of the notification, it may be treated as if an agreement was not obtained from the third user terminal 20C.

Figure 10:
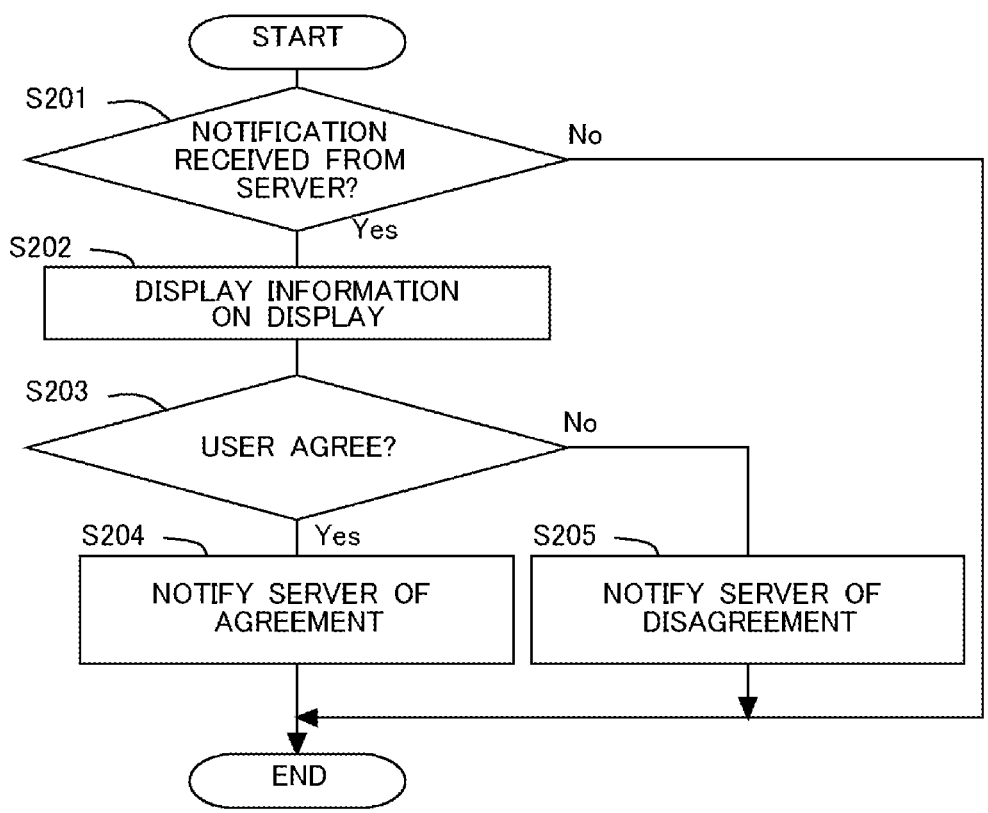
FIG. 10 is a flowchart of processing at the time when the user terminal receives a notification according to the first embodiment.

Next, FIG. 10 is a flowchart of processing when a user terminal 20 receives a notification according to the present embodiment. The processing illustrated in FIG. 10 is executed at each predetermined time interval in the user terminal 20.

In step S201, the control unit 201 determines whether or not information about the physical condition of the target person has been received from the server 30. When an affirmative determination is made in step S201, the processing or routine proceeds to step S202, whereas when a negative determination is made, this routine is ended. In step S202, the control unit 201 displays the information received from the server 30 on the display 25 and also displays, for example, a radio button for allowing the user to select whether or not to agree to go and see the target person.

In step S203, the control unit 201 determines whether or not the user has agreed to go and see the state of the target person. The control unit 201 determines, based on the radio button pressed by the user, whether or not the user has agreed to go and see the state of the target person. When an affirmative determination is made in step S203, the processing proceeds to step S204, whereas when a negative determination is made, the processing proceeds to step S205.

In step S204, the control unit 201 notifies the server 30 that the user has agreed to go and see the state of the target person. On the other hand, in step S205, the control unit 201 notifies the server 30 that the user has not agreed to go and see the state of the target person.

As described above, according to the present embodiment, in cases where an abnormality has occurred in the body of a target person, a notification is transmitted to a notification destination that has been registered in advance in accordance with the physical condition of the target person, thereby making it possible to notify an appropriate party.

Second Embodiment

In a second embodiment, in cases where it is determined that the physical condition of a target person falls into a category other than a category corresponding to a specific notification destination, a notification is transmitted to a user terminal 20 of the specific notification destination, and when request information is received from the specific notification destination, a notification is transmitted to a user terminal 20 of a notification destination corresponding to the category into which the physical condition of the target person falls. Other hardware, etc., is the same as in the first embodiment, and thus the description thereof will be omitted. Here, note that in the following, a case will be described by way of example in which the user terminal 20 of a specific notification destination is a second user terminal 20B.

In this second embodiment, in cases where the physical condition of the target person falls into the first category or the second category, first, a notification is transmitted to a second user terminal 20B, which is a specific user terminal 20. Then, only when request information is received from the second user terminal 20B, a notification is transmitted to a first user terminal 20A or a third user terminal 20C. In the second embodiment, the second user is, for example, a guardian of the target person, and is only one person. The first category or the third category in the second embodiment is an example of a first category of the present disclosure.

Figure 11:
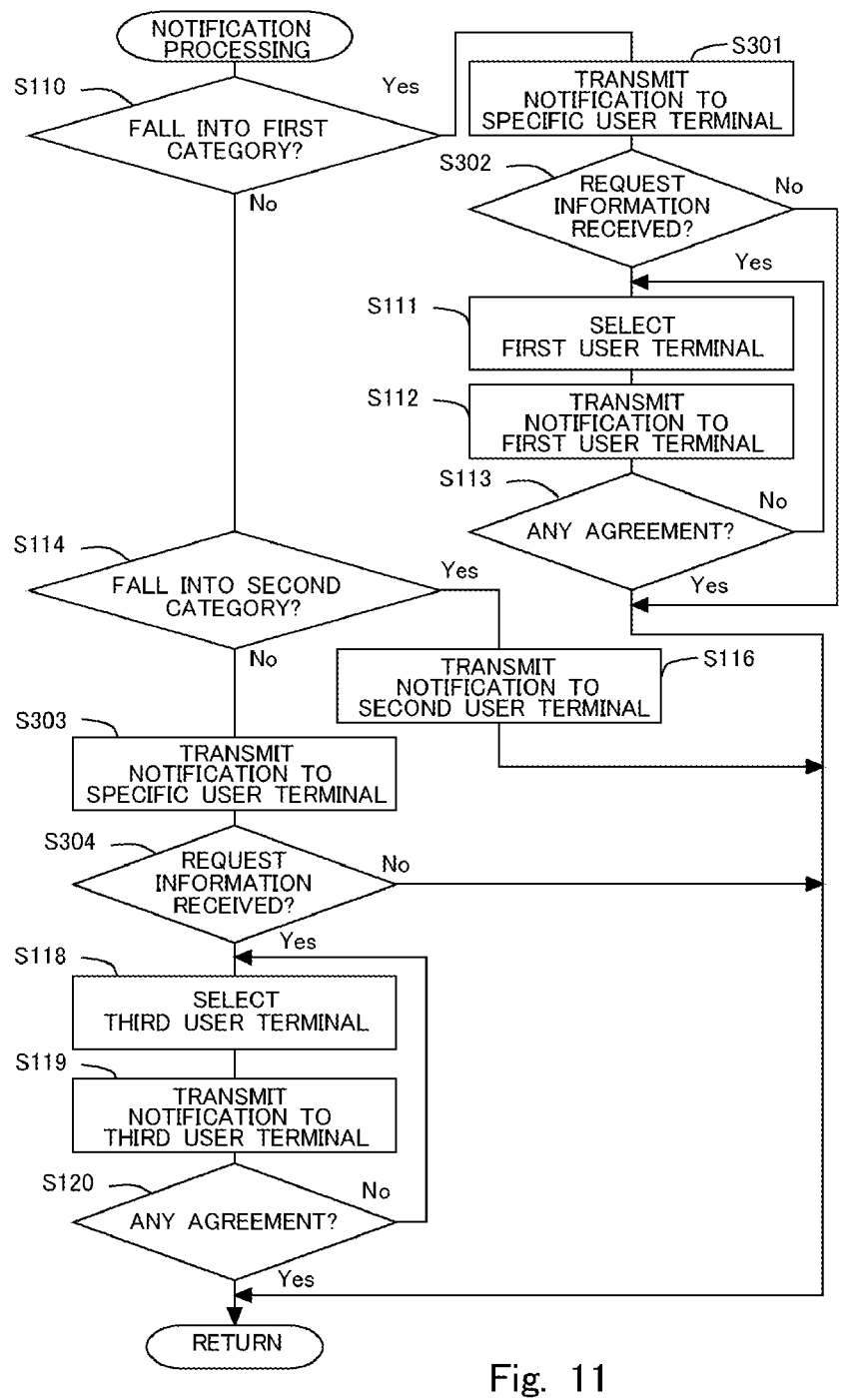
FIG. 11 is a flowchart of notification processing according to a second embodiment.

FIG. 11 is a flowchart of notification processing according to the second embodiment. The notification processing illustrated in FIG. 11 corresponds to the processing of S105 in FIG. 8 that is executed in the server 30. Here, note that those steps in which the same processing is performed as in the routine illustrated in FIG. 9 are denoted by the same reference signs, and the description thereof will be omitted.

In the flowchart illustrated in FIG. 11, when an affirmative determination is made in step S110, the processing proceeds to step S301. In step S301, the control unit 301 transmits a notification to a second user terminal 20B, which is a specific user terminal 20. This notification includes information indicating that the physical condition of the target person falls into the first category, and an inquiry about whether or not to request the first user to go and see the state of the target person. In the second user terminal 20B that has received this notification, the information received from the server 30 is displayed on the display 25, and a radio button, for example, is displayed to allow the second user to select whether or not to request the first user to go and see the state of the target person is displayed. When the second user agrees to request the first user to go and see the state of the target person, request information is transmitted from the second user terminal 20B to the server 30.

In step S302, the control unit 301 determines whether or not the request information has been received. When an affirmative determination is made in step S302, the processing proceeds to step S111, whereas when a negative determination is made, this routine is ended.

In addition, in the routine illustrated in FIG. 11, when an affirmative determination is made in step S114, the processing proceeds to step S116. Note that in the routine illustrated in FIG. 11, the processing illustrated in step S117 of FIG. 9 is omitted, but instead, the processing in step S117 may be executed as illustrated in FIG. 9.

On the other hand, when a negative determination is made in step S114, the processing proceeds to step S303. In step S303, the control unit 301 transmits a notification to the second user terminal 20B, which is the specific user terminal 20. This notification includes information indicating that the physical condition of the target person falls into the third category, and an inquiry about whether or not to request a third user to go and see the state of the target person. In the second user terminal 20B that has received this notification, the information received from the server 30 is displayed on the display 25, and a radio button, for example, is displayed to allow the second user to select whether or not to request the third user to go and see the state of the target person. When the second user agrees to request the third user to go and see the state of the target person, request information is transmitted from the second user terminal 20B to the server 30.

In step S304, the control unit 301 determines whether or not the request information has been received. When an affirmative determination is made in step S304, the processing proceeds to step S118, whereas when a negative determination is made, this routine is ended.

In this way, a notification is transmitted to the first user or the third user only when the second user makes a request, so that it is possible to prevent the notification from being transmitted to the first user or the third user more than necessary.

Other Embodiments

The above-described embodiments are merely examples, but the present disclosure can be implemented with appropriate modifications without departing from the spirit thereof.

The processing and devices, units, etc. described in the present disclosure can be freely combined and implemented as long as no technical contradiction occurs.

In addition, the processing described as being performed by a single device or unit may be shared and performed by a plurality of devices or units. Alternatively, the processing described as being performed by different devices or units may be performed by a single device or unit. In a computer system, a hardware configuration (server configuration) for realizing each function thereof can be changed in a flexible manner. For example, the camera 10 or the user terminal 20 may include all or a part of the functions of the server 30.

The present disclosure can also be realized by supplying to a computer a computer program in which the functions described in the above-described embodiments are implemented, and reading out and executing the program by one or more processors included in the computer. Such a computer program may be provided to the computer by a non-transitory computer readable storage medium that can be connected to a system bus of the computer, or may be provided to the computer via a network. The non-transitory computer readable storage medium includes, for example, any type of disk such as a magnetic disk (e.g., a floppy (registered trademark) disk, a hard disk drive (HDD), etc.), an optical disk (e.g., a CD-ROM, a DVD disk, a Blu-ray disk, etc.) or the like, a read-only memory (ROM), a random-access memory (RAM), an EPROM, an EEPROM, a magnetic card, a flash memory, an optical card, or any type of medium suitable for storing electronic commands or instructions.

What is claimed is:

1. An information processing apparatus including a controller configured to perform:
   determining, based on information obtained from a sensor configured to detect a physical condition of a target person, which of a plurality of predetermined categories the physical condition of the target person falls into;
   transmitting a notification corresponding to the physical condition of the target person to a terminal of a notification destination that corresponds to a category into which the physical condition of the target person is determined to fall, wherein terminals of notification destinations are set for the plurality of categories, respectively;
   obtaining information indicating a current situation of each of a plurality of candidates for the terminal of the notification destination, in cases where there are the plurality of candidates for the notification destination terminal that corresponds to the category into which the physical condition of the target person is determined to fall, the information indicating the current situation is information about a schedule from each of the terminal candidates; and
   determining the terminal of the notification destination based on the current situation of each of the plurality of candidates for the terminal of the notification destination.

2. The information processing apparatus according to claim 1, wherein
   the controller performs:
   transmitting a notification to a terminal of a specific notification destination in cases where it is determined that the physical condition of the target person falls into a first category other than a category corresponding to the specific notification destination, and transmitting a notification to a terminal of a notification destination corresponding to the first category when request information is received from the specific notification destination.

3. The information processing apparatus according to claim 2, wherein
   the controller selects, as the specific notification destination, a person who has an obligation to guard the target person.

4. The information processing apparatus according to claim 1, wherein
   the controller performs:
   storing the information obtained from the sensor in a storage unit when it is determined that the physical condition of the target person falls into any one of the plurality of predetermined categories.

5. The information processing apparatus according to claim 1, wherein
   the controller performs:
   transmitting to the terminal of the notification destination a notification including a request to go and see the target person; and
   newly determining a terminal of another notification destination in cases where there is no response from the terminal of the notification destination to an effect of agreeing to go and see a state of the target person.

6. The information processing apparatus according to claim 1, wherein
   the plurality of predetermined categories include categories classified according to a degree of illness or injury of the target person.

7. The information processing apparatus according to claim 1, wherein
   the plurality of categories include a category corresponding to transport of the target person to a hospital.

8. An information processing method for causing a computer to perform:
   determining, based on information obtained from a sensor configured to detect a physical condition of a target person, which of a plurality of predetermined categories the physical condition of the target person falls into;
   transmitting a notification corresponding to the physical condition of the target person to a terminal of a notification destination that corresponds to a category into which the physical condition of the target person is determined to fall, wherein terminals of notification destinations are set for the plurality of categories, respectively;
   obtaining information indicating a current situation of each of a plurality of candidates for the terminal of the notification destination, in cases where there are the plurality of candidates for the notification destination terminal that corresponds to the category into which the physical condition of the target person is determined to fall, the information indicating the current situation is information about a schedule from each of the terminal candidates; and
   determining the terminal of the notification destination based on the current situation of each of the plurality of candidates for the terminal of the notification destination.

9. The information processing method according to claim 8, wherein
   the computer is caused to perform:
   transmitting a notification to a terminal of a specific notification destination in cases where it is determined that the physical condition of the target person falls into a first category other than a category corresponding to the specific notification destination, and transmitting a notification to a terminal of a notification destination corresponding to the first category when request information is received from the specific notification destination.

10. The information processing method according to claim 9, wherein
    the computer is caused to perform:
    selecting, as the specific notification destination, a person who has an obligation to guard the target person.

11. The information processing method according to claim 8, wherein
    the computer is caused to perform:
    storing the information obtained from the sensor in a storage unit when it is determined that the physical condition of the target person falls into any one of the plurality of predetermined categories.

12. The information processing method according to claim 8, wherein
the computer is caused to perform:
transmitting to the terminal of the notification destination a notification including a request to go and see the target person; and
newly determining a terminal of another notification destination in cases where there is no response from the terminal of the notification destination to an effect of agreeing to go and see a state of the target person.

13. A system comprising:
a storage unit configured to store a relationship between a physical condition of a target person and a plurality of categories and a relationship between the plurality of categories and terminals of notification destinations;
a sensor configured to detect the physical condition of the target person; and
a controller configured to perform:
determining, based on information obtained from the sensor, which of the plurality of categories the physical condition of the target person falls into; and
transmitting a notification corresponding to the physical condition of the target person to a terminal of a notification destination corresponding to a category into which the physical condition of the target person is determined to fall;
obtaining information indicating a current situation of each of a plurality of candidates for the terminal of the notification destination, in cases where there are the plurality of candidates for the notification destination terminal that corresponds to the category into which the physical condition of the target person is determined to fall, the information indicating the current situation is information about a schedule from each of the terminal candidates; and
determining the terminal of the notification destination based on the current situation of each of the plurality of candidates for the terminal of the notification destination.

\* \* \* \* \*